United States Patent
Biebricher et al.

(10) Patent No.: US 9,952,421 B2
(45) Date of Patent: Apr. 24, 2018

(54) APPARATUS AND METHOD FOR CONTROLLING A PLURALITY OF OPTICAL TRAPS

(71) Applicant: Stichting Vu, Amsterdam (NL)

(72) Inventors: Andreas Sebastian Biebricher, Amsterdam (DE); Andrea Candelli, Amsterdam (IT); Iddo Heller, Amsterdam (NL); Niels Laurens, Amsterdam (NL); Erwin Johannes Gerard Peterman, Amsterdam (NL); Gijs Jan Lodewijk Wuite, Amsterdam (NL)

(73) Assignee: Stichting VU, Amsterdam (NL)

( * ) Notice: Subject to any disclaimer, the term of this patent is extended or adjusted under 35 U.S.C. 154(b) by 0 days.

(21) Appl. No.: 15/549,832

(22) PCT Filed: Feb. 4, 2016

(86) PCT No.: PCT/NL2016/050079
§ 371 (c)(1),
(2) Date: Aug. 9, 2017

(87) PCT Pub. No.: WO2016/129994
PCT Pub. Date: Aug. 18, 2016

(65) Prior Publication Data
US 2018/0024342 A1    Jan. 25, 2018

(30) Foreign Application Priority Data

Feb. 9, 2015 (NL) ..................................... 2014262

(51) Int. Cl.
G02B 21/32     (2006.01)
G02B 27/14     (2006.01)
(Continued)

(52) U.S. Cl.
CPC .......... G02B 21/32 (2013.01); B01L 3/50273 (2013.01); B01L 3/502761 (2013.01);
(Continued)

(58) Field of Classification Search
CPC ...................................................... G02B 21/32
See application file for complete search history.

(56) References Cited

U.S. PATENT DOCUMENTS

| 2010/0099076 A1 | 4/2010 | Mao et al. |
| 2013/0100461 A1* | 4/2013 | Wischnewski ......... G02B 21/32 356/614 |

FOREIGN PATENT DOCUMENTS

| EP | 1 850 182 A2 | 10/2007 |
| EP | 1 855 141 A1 | 11/2007 |

OTHER PUBLICATIONS

Koen, Visscher, et al., "Construction of Multiple-Beam Optical Traps with Nanometer-Resolution Position Sensing," IEEE Journal of Selected Topics in Quantum Electronics, IEEE Service Center, Piscataway, NJ (USA), vol. 2, No. 4, Dec. 1, 1996, pp. 1066-1076.

* cited by examiner

Primary Examiner — David Porta
Assistant Examiner — Hugh H Maupin
(74) Attorney, Agent, or Firm — Kilpatrick Townsend & Stockton LLP

(57) ABSTRACT

The present disclosure relates to an apparatus (100) and method for controlling a plurality of simultaneously active optical traps (OT1,OT2,OT3). In one method, trapping beams (TB1,TB2,TB3) are provided and redirected for individually controlling a respective position (X,Y) of optical traps (OT1,OT2,OT3) formed by focusing of the redirected trapping beams in a sample volume (SV). Light (L11,L20) from the sample volume (SV) corresponding to the optical traps is received. A path of a detector beam (AB)
(Continued)

is overlapped with one of the trapping beams (TB3), wherein the detector beam has a distinct wavelength ($\lambda A$) from that of the overlapping trapping beam (TB3). In one channel, the light from the sample volume is filtered according to wavelength, and only the filtered light having the wavelength ($\lambda A$) of the detector beam (AB) is measured.

16 Claims, 5 Drawing Sheets

(51) Int. Cl.
    *G02B 26/08*     (2006.01)
    *G02B 27/28*     (2006.01)
    *G02B 21/16*     (2006.01)
    *G02B 21/18*     (2006.01)
    *G02B 21/36*     (2006.01)
    *G01N 21/64*     (2006.01)
    *B01L 3/00*     (2006.01)
    *G02B 27/10*     (2006.01)
(52) U.S. Cl.
    CPC ..... *G01N 21/6428* (2013.01); *G01N 21/6458* (2013.01); *G02B 21/16* (2013.01); *G02B 21/18* (2013.01); *G02B 21/361* (2013.01); *G02B 26/0816* (2013.01); *G02B 27/106* (2013.01); *G02B 27/141* (2013.01); *G02B 27/283* (2013.01); *B01L 2200/0663* (2013.01); *B01L 2300/0654* (2013.01); *B01L 2400/0454* (2013.01); *G01N 2021/6439* (2013.01)

APPARATUS AND METHOD FOR CONTROLLING A PLURALITY OF OPTICAL TRAPS

CROSS-REFERENCES TO RELATED APPLICATIONS

This application is a US National Phase of PCT/NL2016/050079, filed Feb. 4, 2016, which claims priority to Netherlands Application No. 2014262, filed Feb. 9, 2015, the entireties of which are incorporated by reference herein.

TECHNICAL FIELD AND BACKGROUND

The present disclosure relates to optical tweezers, in particular an apparatus and method for controlling a plurality of optical traps.

Optical tweezers may be considered one of the pillars of the single-molecule toolbox. The method typically comprises application of one or more highly focused laser beams ("trapping beams") in a sample volume to form optical traps. The physical principle can be explained by the momentum transfer (force) between the incident photons and the trapped objects that occurs upon refraction. For example, when the geometry of the experiment includes a spherical object ("microsphere" or "bead") having a refraction index higher than the surrounding medium (glass and water for example) the generated optical forces creates a stable three dimensional optical trap. Optical tweezers can be used for example in remote manipulating of micrometer-sized objects. One application comprises attaching a molecular strand such as a DNA molecule between two optically trapped microspheres. In this way it is possible to manipulate and control the conformation of the DNA as well as apply and measure forces on it. This information can be used to study the DNA's mechanical properties and its interaction with proteins.

Traditionally, one or two optical traps are used at a time. However, in many biological circumstances, proteins interact with multiple sections of DNA at the same time (e.g. proteins that repair DNA breaks or are involved in DNA compaction by forming loops in DNA). Such interactions cannot be studied accurately and in a controllable way with only two optical traps. The canonical optical tweezers implementation does not allow to position different DNA molecules in contact in a controllable way while simultaneously measuring the tension on each of them. Furthermore, the data throughput of such implementations is low, since only one DNA molecule is studied at a time.

There are reports of instruments that are able to manipulate different DNA molecules at the same time. See for example, M. C. Noom, B. van den Broek, J. van Mameren, G. J. L. Wuite; "Visualizing single DNA-bound proteins using DNA as a scanning probe"; Nature Methods, 4, 1031-1036 (2007). This prior art involves a design in which the optical tweezers is time-shared between multiple locations (the position of a single laser beam is alternated among separate locations using acoustical-optical deflectors-AOD), thereby producing multiple optical traps. However, in time-shared optical tweezers the trapping in each of the positions is not continuous in time, making them unstable, their force-calibration problematic and in general not suitable for many scientific applications.

As another example, see I. De Vlaminck, M. T. J. van Loenhout, L. Zweifel, J. den Blanken, K. Hooning, S. Hage, J. Kerssemakers, and C. Dekker; "Mechanism of homology recognition in DNA recombination from dual-molecule experiments"; Molecular Cell, 46, 616 (2012). In this prior art dual optical tweezers are combined with Magnetic tweezers. In the configuration one of the DNA molecules is anchored between a magnetic sphere and a glass surface. The second DNA molecule is held in solution between the two optically trapped spheres. However, the use of surface-bound DNA in the Magnetic tweezers limits the flexibility and ease of use of the instrument, making this approach for example less compatible with a microfluidics platform.

Accordingly, there remains a desire to continuously manipulate and monitor a multitude of optical traps in a reliable fashion.

SUMMARY

According to one aspect, the present disclosure provides an apparatus for controlling a plurality of optical traps. The apparatus comprises trapping beam optics configured to provide a plurality of simultaneously active trapping beams. The apparatus further comprises controllable optics, such as controllable mirrors, configured to receive and redirect the trapping beams for controlling a respective position of at least three optical traps. The optical traps are e.g. formed by focusing of the redirected trapping beams in a sample volume. The apparatus may comprise or be coupled to one or more light detectors such as quadrant photodiodes or position sensitive detectors. Each detector is configured to receive a respective portion of light from the sample volume corresponding to a respective one of the optical traps. The apparatus comprises detector beam optics configured to overlap a path of a detector beam with one of the trapping beams. The detector beam has an optical property that makes it distinguishable from the trapping beam it is overlapped with. For example, the detector beam has a distinct wavelength from one or more of the trapping beams. For example, a wavelength filter is disposed in a light path between the sample volume and one of the light detectors. The wavelength filter is configured to pass light with the wavelength of the detector beam to the detector.

According to another or further aspect, the present disclosure provides a method for controlling a plurality of optical traps. The method comprises providing a plurality of simultaneously active trapping beams. The method further comprises redirecting the trapping beams for individually controlling a respective position of a plurality of optical traps formed by focusing of the redirected trapping beams in a sample volume. Light received from the sample volume may correspond to a status of the optical traps. A detector beam, e.g. having a distinct wavelength, is overlapped with one of the trapping beams. In a one detection path, the light from the sample volume is filtered according to wavelength. Accordingly, only the filtered light having the wavelength of the detector beam can be measured (by the detector) and used for monitoring the optical trap. The method can be advantageously implemented e.g. in the apparatus described above or otherwise. The various embodiments described in relation to the apparatus can also be combined with the method and vice versa.

Traditionally, a pair of optical tweezers is monitored by distinguishing the trapping light based on their orthogonal polarizations. However, when adding a third trapping beam, its polarization cannot be distinguished from that of the first or second beam, which means only one of the three traps can be distinguished. The inventors find that by overlapping an detector beam with an optical trapping beam, the properties (e.g. force) of the optical trap formed by the trapping beam can be monitored by measuring the light of the detector beam instead. For example, the detection beam can be used to control the position of the trap. For example, by using separate detector beams, three or more optical traps can be used while two or more of the traps can be monitored.

By providing a first trapping beam with a first polarization, and the other trapping beams with an orthogonal second polarization, the first beam can be separately monitored, e.g. via a polarization filter. By overlapping the detector beam with one of the other trapping beams having the orthogonal polarization, a second optical trap can be separately monitored, also when using three or more optical traps in total. For example, by using a detector beam with different wavelength, the limitations of separating optical traps having at most two different polarizations, can be overcome. By having one trapping beam with a distinct polarization, while overlapping one or more of the other trapping beams with one or more detector beams, less detector beams are necessary. For example, to monitor two of the three or more optical traps, only one detector beam is needed.

Advantageously, the light of three or more trapping beams can have the same wavelength, e.g. generated by a single light source. For example, by using one or more beam splitters the light from a trapping light source can be divided into two or more of the trapping beams. By providing a polarizing beam splitter, a source beam can be divided into a first and second trapping beam having orthogonal polarization. Further trapping beams with the same polarization direction can be generated, e.g. by non-polarizing beam splitters, e.g. comprising a semi-transparent reflection surface. Before sending the beams to the sample volume, the beams may be combined, e.g. using polarizing and/or non-polarizing beam splitters. For example, a non-polarising beam combiner, e.g. cube, can be used to combine beams having the same wavelength and polarization.

Advantageously, the detector beam can have a lower power than the trapping beam. A beam combiner can be used to overlap the detector beam with one of the trapping beams. By overlapping the beams before a controllable mirror, any movement of the trapping beam is automatically followed by corresponding movement of the detector beam. For example, a dichroic mirror can be used to combine the beams. Alternatively, or in addition, the detector beam can be inserted at a beam splitter before the controllable mirror. If necessary, a filter can be placed to ensure only one of the trapping beams is overlapped with the detector beam light. By providing the detector light beam with the same polarization as the trapping beam it is overlapped with, the detector beam can follow the trapping beam also via polarization dependent optical elements.

The trapping beams can be focused in the sample volume to form the optical traps, e.g. by means of an objective or other lens between the controllable mirrors and the sample volume. Advantageously, the objective lens can also be used to direct other beams into the sample volume, e.g. an excitation beam of a fluorescence microscope. Furthermore by providing a telescope between the controllable mirrors and the sample volume, angular movements resulting from rotation of the controllable mirrors can be converted into lateral displacement in the sample volume. Preferably, optical components used to focus the trapping and detector beams are as much as possible wavelength independent, in particular when using a different wavelength detector beam. Alternative or in addition to lenses, curved e.g. parabolic or spherical mirrors can be used to focus and defocus the beams.

By providing at least four optical traps, two molecular strands can be manipulated independently. Advantageously, by monitoring one optical trap for each strand, the force on the strand can be adequately monitored. It is thus not necessary to monitor the force of all four traps, and a relatively simple optical setup can be used, e.g. using only one detector beam. For example the light detectors may monitor at least two of the optical traps by measuring the light with the first polarization at a first detector and measuring the light with the wavelength of the detector beam at a second detector. By providing individual focus control (e.g. separate telescopes) for a first pair of optical traps and a second pair of optical traps, two molecular strands can be moved with respect to each other in three dimensions. For example, a position of a focal plane of a first and second of the optical traps can be shifted with respect to a focal plane of a third and fourth of the optical traps. Alternatively, or in addition, also more than two traps can be used per strand. For example three traps can be used at different locations along a single strand, e.g. to fold the strand back on itself.

It will be appreciated that the present disclosure can be applied to monitor even further optical traps by providing multiple detector beams and/or providing orthogonally polarized detector beams. Two or more detector beams can e.g. be distinguished by having a distinct wavelength and/or polarization with respect to each other. For example, two optical traps can be monitored by overlapping a first polarization of a detector beam with one of the trapping beams and overlapping a second polarization of a detector beam with another of the trapping beams. The differently polarized detector beams can be isolated by a combination of wavelength and polarization filtering. In this scheme, a third optical trap can be monitored without detector beam, by isolating the distinct (first) polarization and wavelength of that trapping beam. Instead of, or alternative to using different polarized detector beams, also different wavelengths can be used for different detector beams. The detector beams do not require much power, and may be generated, e.g. by a separate laser source and/or by non-linear optics from the same laser source as the trapping beams.

To monitor further properties e.g. interactions between or within molecular strands held by the optical traps, imaging techniques such as fluorescence microscopy or other types of (optical) labelling can be used. For example, an excitation light source can be configured to provide an excitation beam to the sample volume wherein an excitation of a fluorophore on the molecular strand by the excitation beam results in a fluorescence response. A fluorescence detector can be configured for recording the fluorescence response as a function of position in the sample volume. Advantageously, it is found that the present techniques can be combined with focused excitation of the fluorophores on the molecular strand. Because the one or more strands are held between defined positions of the optical traps, the excitation focus can scan between the said positions of the optical traps. To improve background rejection, a confocal setup can be used. Focal spot illumination can also enhance resolution of the molecular imaging. To further improve resolution, a depletion beam can be used to cause stimulated emission depletion (STED) of the excitation of the fluorophore according to a depletion profile, e.g. donut. By providing the sample volume in a sample cell, e.g. flow cell, the environment of the molecular strands can be controlled. For example two DNA molecules can be held together while labelled proteins are brought in proximity to the molecules by a microfluidic flow cell. It will be appreciated that the present instruments allows controlled manipulation and monitoring of multiple molecular strands such as DNA while measuring the interactions between the strands and/or the environment.

The apparatus or method as described herein can be used for example for positioning a first molecular strand with respect to a second molecular strand. Such method may include providing at least four trapping beams e.g. in a manner as described above. Two positions along a length of the first molecular strand can be trapped with the first and second optical traps while the second strand can be trapped by the third and fourth optical traps. Advantageously, at least two of the four traps can be monitored, e.g. the force measured. The force or tension on each strand can thus be monitored separately. The strands can e.g. be captured by attaching microspheres at specific locations along the strand or at one or both ends of the strand. When a first part of the strand is captured, the strand can e.g. be flow stretched such that a second part is directed towards a second trap, positioned downstream of the first trap. This can be done sequentially or simultaneously for multiple pairs of traps. To check if a strand has been captured, e.g. the pair of traps can be moved apart and the force on the strand measured. When two strands have been captured, one or more of the optical traps can be set to have the molecular strands cross or intersect with each other. For example the first and second strands can be manipulated in three dimensions to cross each other and then brought together to form a point of intersection. The point of intersection at each of the strands can be controlled by the relative positioning of the traps. Alternatively, or in addition, markers can be placed at specific locations on the one or more strands to facilitate the relative aligning of the strands. Further molecules such as proteins can be provided in the sample volume interacting with the first and/or second molecular strands. As discussed above, the interactions of the molecular strands with each other and/or with further molecules can be monitored by imaging techniques such as fluorescent microscopy and/or force displacement measurements. For example an excitation focus in the sample volume can be scanned over the molecular strands, e.g. over a line between a pair of optical traps and/or around the point of intersection.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
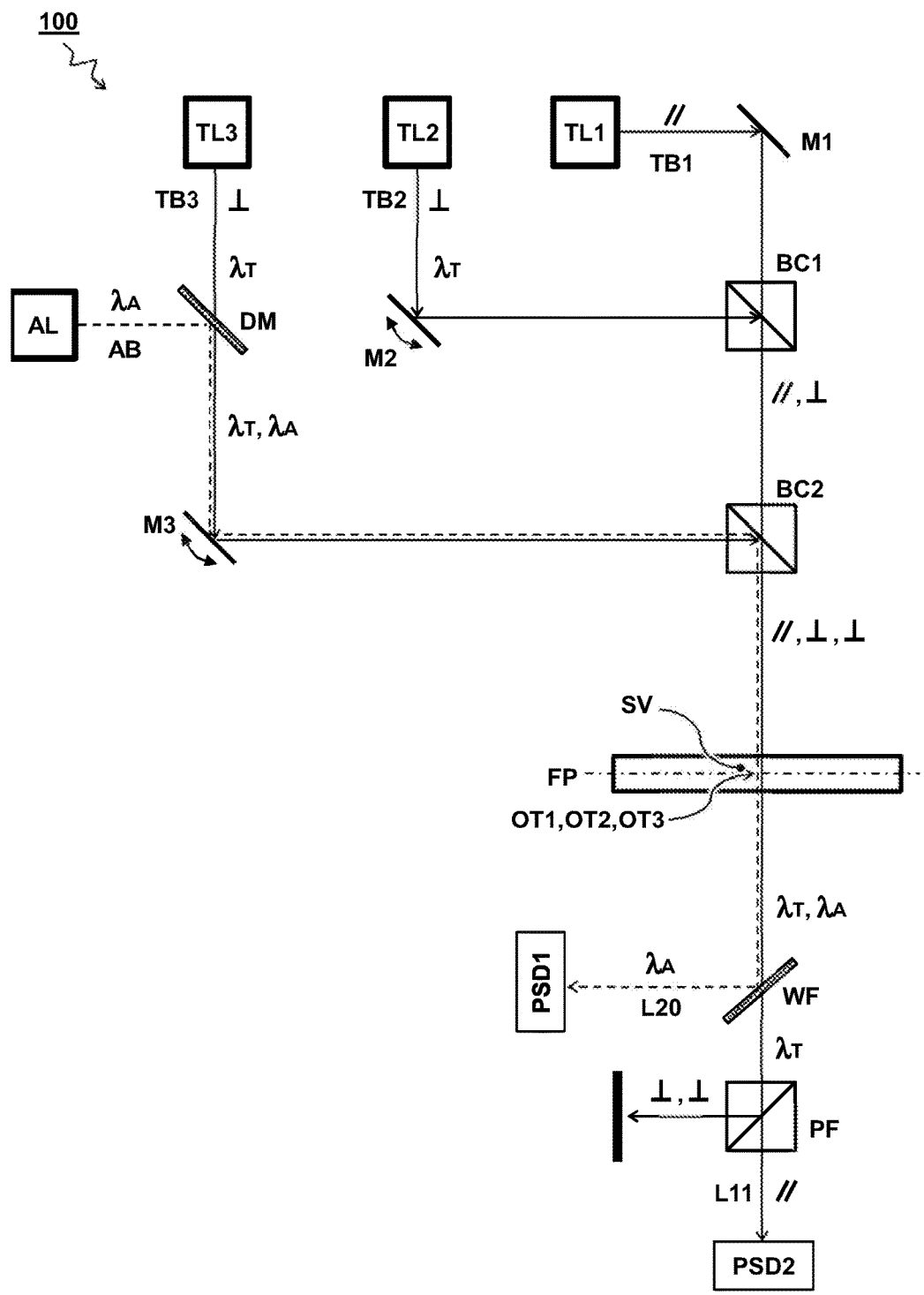
FIG. 1 schematically shows an example embodiment of an apparatus for controlling a plurality of optical traps.

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The present disclosure enables generation and control of multiple optical traps in three dimensions in a continuous way (without the need of acoustical-optical deflectors-AOD). In some aspects, the disclosure may be applied as a method for manipulating multiple (at least 2) DNA molecules in three dimensions using optical tweezers technology. Two or more DNA molecules can be manipulated independently and in a dynamic fashion while monitoring the force acting on each of them. Of course the application of the disclosure is not restricted to DNA, but applications can also be envisioned to other linear molecules or molecular assemblies, including, but not limited to, proteins, polysaccharides, organic polymers, carbon nanotubes and fibrous inorganic materials. When imaging the molecular strand, also molecules attaching to the strand (e.g. proteins) can be imaged. The optical design developed for the present methods and systems may permit the integration with (fluorescence) microscopy and microfluidics approaches. This integration can allow improved studies in the field of DNA transactions such as organization and repair. It may allow to visualize and sense how proteins mediate the interactions between DNA molecules.

Further advantages may include the possibility of increasing the data-throughput of single-molecule measurements by using simultaneously more than one DNA substrate in the same experiment. Furthermore, the methods may be based on a combination of power, wavelength, and polarization splitting. This enables to distribute equally the laser light across multiple locations while keeping each trap continuously present at each position (in contrast to time-sharing approaches). Advantageously, all optical traps present in the sample can have equal performances and the bead (microsphere) is continuously trapped. Because the DNA molecules are suspended in solution it is possible to trigger the biochemical reaction using for example a microfluidics approach. The individual DNA molecule(s) and/or the fluorescence protein can be visualized while interacting with multiple DNA molecules simultaneously.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1 shows an embodiment of an apparatus 100 for controlling a plurality of optical traps.

In the embodiment shown, the apparatus comprises trapping beam optics TL1, TL2, TL3 configured to provide a plurality of simultaneously active trapping beams TB1, TB2, TB3. The phrase "simultaneously active" is used herein to indicate that each of the trapping beams can be active at the same time. This allows the beams to be continuously active without intermission. A configuration of continuously active trapping beams may be distinguished e.g. from a configuration of time-shared beams that are intermittently active at different times. By providing continuously active trapping beams, the corresponding optical traps can provide a continuous force and/or improved reliability.

The apparatus further comprises mirrors M1, M2, M3 configured to receive and redirect the trapping beams TB1, TB2, TB3 for individually controlling a respective position of a plurality of optical traps OT1, OT2, OT3 formed by focusing of the redirected trapping beams in a sample volume SV. Preferably at least two of the three mirrors are controllable to determine a relative position of the beams. For example, the mirror M1 can be fixed. Alternatively, all mirrors are controllable. Of course the controllable mirrors may comprise any optical and mechanical components for controlling a direction and/or position of the trapping beams. The mirrors are preferably controlled automatically. Alternative to a reflective surface, also refractive elements can be used to redirect a beam. Typically, the controllable mirror includes an actuator, e.g. piezo element.

In the embodiment shown, the apparatus comprises light detectors PSD1,PSD2. Each detector is configured to receive a portion of light L11, L20 from the sample volume SV corresponding to one of the optical traps OT3. While a single detector can be provided, preferably multiple detectors are used to monitor a respective number of optical traps. Detectors can also be partly or fully integrated. For example, a single detection surface may detect multiple beams, e.g. at different sensor positions. The detector may include any component capable of measuring light from the trapping beams and/or detector beams. For example, a pixel or quadrant detector or position sensitive detector can be used to determine a position of a beam.

For example, the light pattern measured by the detector may correspond to the influence of an object such as a microsphere in or near the optical trap. In one embodiment, a position of a bead or microsphere in the optical trap is determined using back-focal-plane (BFP) interferometry. In BFP interferometry, light scattered by the bead interferes with the other light of the trapping beam in the back-focal-plane of the condenser (e.g. condenser lens CL). A position of the bead in the trap can be inferred from this interference pattern on the detector. From the position of the bead in the trap, a force exerted on the bead can be calculated. In an embodiment where the beads are larger than the focus, all the light travels through the bead and the bead works as a lens and displaces the (total) beam if it is displaced from the trapping focus. Alternatively or in addition to the BFP detection, the beads can also be imaged using a regular lighting and camera. For example, in the embodiment of FIG. 2, an LED light source is used to illuminate the beads and the resulting picture is imaged on a camera CAM.

In the embodiment shown, the apparatus comprises detector beam optics AL configured to overlap a path of a detector beam AB with one of the trapping beams TB3. Typically, alignment is achieved by overlapping two beams at a specific position and providing the beams with the same direction. In one embodiment, as shown, the detector beam has a distinct wavelength $\lambda A$ from that of the overlapping trapping beam TB3. In one embodiment, the light detector PSD1 is configured to monitor an optical trap by measuring the detector beam having the distinct wavelength A. Alternatively, or in addition, the detector beam may distinguished in other ways from the trapping beam, e.g. by polarization and/or (intensity) (temporal) modulation. The detector beam can have a lower power than the trapping beam, e.g. less than 10 percent, less than 5 percent, or even less, e.g. between 0.001 and 10 percent. In the embodiment shown, the apparatus comprises a wavelength filter WF disposed in a light path between the sample volume SV and the light detector PSD1. The wavelength filter WF is configured to pass light with the wavelength $AA$ of the detector beam AB to one of the light detectors PSD1.

In the embodiment shown, the trapping beam optics TL1, TL2, TL3 are configured to provide at least three trapping beams TB1, TB2, TB3. A first trapping beam TB1 is provided with a first polarization (//), and the other trapping beams TB2,TB3 are provided with a second polarization ($\perp$), orthogonal (e.g. at or around 90 degrees) to the first polarization (//). The trapping beam optics are shown in the figure as separate components, but they may also be partly or fully integrated. The trapping beam optics may include any component or combination of components capable of providing the beams at the desired polarizations. The components may include one or more light sources, polarizers, beam splitters, wave plates, etcetera. In one embodiment, the detector beam optics AL are configured to overlap the detector beam AB with one of the other trapping beams TB3 having the second polarization ($\perp$). In one embodiment, the wavelength $\lambda A$ of the detector beam is distinct from that of the trapping beams TB2,TB3. In one embodiment, the apparatus comprises a polarization filter PF disposed in a light path between the sample volume SV and a second light detector PSD2, and configured to pass light with the first polarization (//) to the second light detector PSD2.

In the embodiment shown, the apparatus comprises beam combiners BC1, BC2 disposed in a light path between the controllable mirrors M1, M2, M3 and the sample volume SV. The beam combiners are configured to receive and combine the trapping beams TB1, TB2, TB3 from the controllable mirror and direct the combined trapping beams towards the sample volume SV. The beam combiners may e.g. comprise beam splitters in reverse configuration. In one embodiment, the detector beam optics comprises a beam combiner DM disposed in a light path between a trapping light source TL3 and at least one of the controllable mirrors M3 corresponding to one of the other trapping beams TB3 with the second polarization ($\perp$). The beam combiner comprises a reflective surface configured to overlap a transmission of one of the alignment or trapping beam with a reflection of the other of the alignment or trapping beam. For example, in the embodiment shown, the detector beam optics comprises a dichroic mirror DM disposed in a light path of one of the other trapping beams TB3 before the respective controllable mirror M3. The dichroic mirror DM is configured to reflect one of the detector beam AB or trapping beam TB3 while transmitting the other.

In one embodiment, the apparatus comprises a non-polarising beam combiner BC2 configured to combine two or more trapping beams having the same wavelength and polarization. In another or further embodiment, a non-polarising beam combiner BC2 is configured to combine three or more trapping beams having the same wavelength. Because the beam combiner BC2 is non-polarizing it does not matter what the polarization is of the beams to be combined. On the contrary, a polarizing beam combiner (e.g. BC1 in FIG. 1) can only be used to combine two beams with different polarizations. Similarly, a dichroic mirror DM can only be used to combine beams having different wavelength. While the non-polarizing beam combiner, e.g. beam cube, may result in some loss of beam power (due to reflection), the configuration can advantageously provide accurate combination and overlap of three or more beams with the same wavelength. It will be appreciated that the non-polarizing beam combiner thus provides particular benefit for the present configuration featuring a plurality of three or more simultaneously active optical traps.

Figure 2:
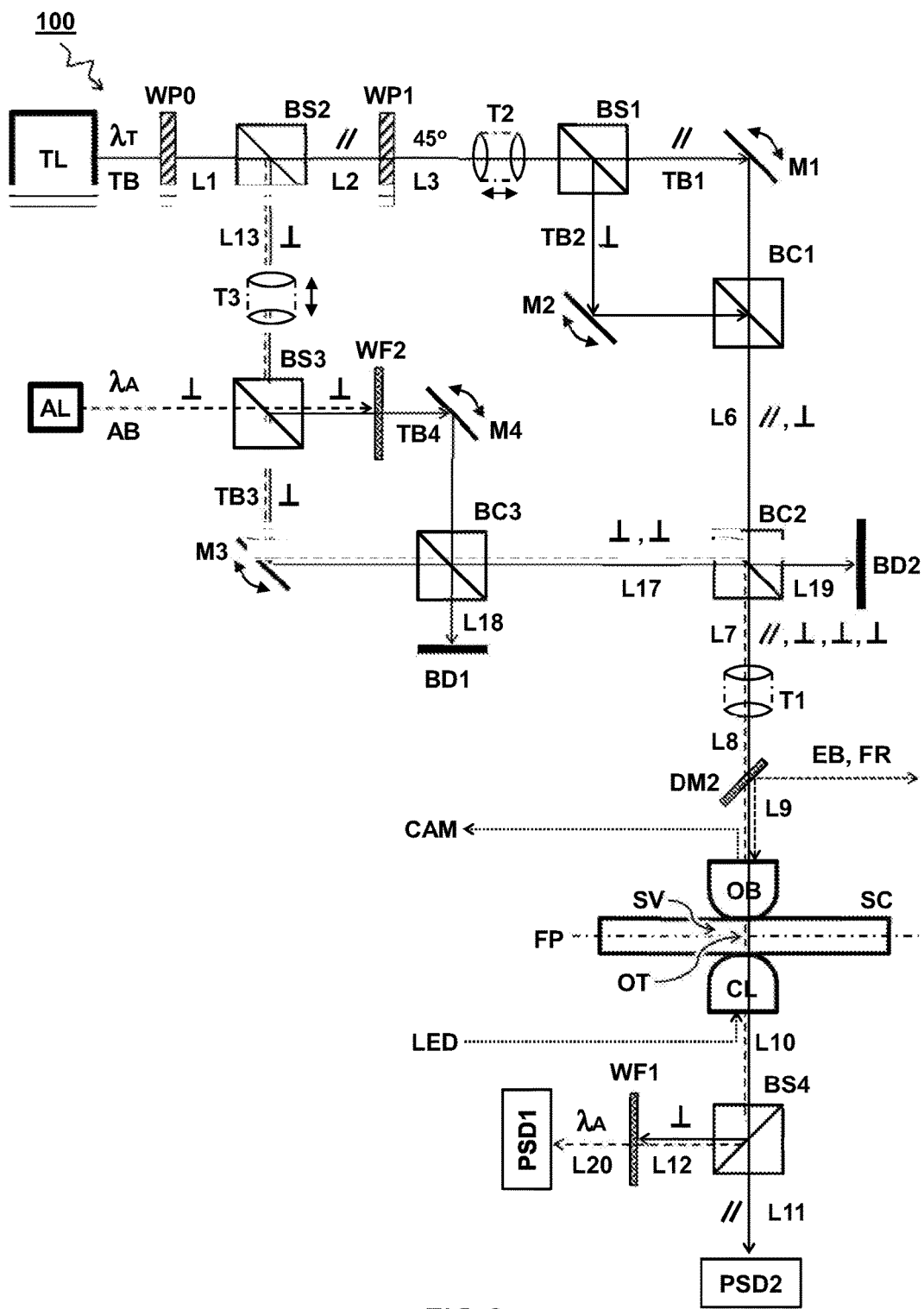
FIG. 2 schematically shows a more elaborate example.

FIG. 2 shows another embodiment of an apparatus 100 for controlling a plurality of optical traps.

In the embodiment shown, the trapping beam optics comprise one or more beam splitters BS1, BS2, BS3. The beam splitters are configured to receive and split a beam of light L1, L3, L13 from a trapping light source TL into two or more of the trapping beams TB1, TB2, TB3 and direct the trapping beams TB1, TB2, TB3 toward the respective controllable mirrors M1, M2, M3. In one embodiment, at least one of the beam splitters BS1 comprises a polarization dependent reflection surface configured to split the beam of light L3 from the trapping light source into the first TB1 of the trapping beams having the first polarization (//), and one of the other trapping beams TB2 having the second polarization ($\perp$). In another or further embodiment at least one of the beam splitters BS3 comprises a semi-transparent reflection surface configured to split the beam of light L13 from the trapping light source into two of the other trapping beams TB3,TB4 having the second polarization ($\perp$). In one embodiment, a beam splitter BS3 for splitting light from the trapping light source TL is configured to receive the detector beam AB and combine the detector beam with at least one of the split output beams. Optionally, a wavelength filter WF2 can be placed in one of the beams to prevent propagation of the detector beam with the fourth trapping beam TB4.

The apparatus may also include one or more beam combiners BC1, BC2, BC3. In one embodiment, at least one of the beam combiners BC1 comprises a polarization dependent reflection surface configured to combine the first TB1 of the trapping beams with one or more of the other trapping beams TB2,TB3. For example, the beam combiner BC2 may comprise a polarizing beam splitter in reverse configuration. In one embodiment, at least one of the beam combiners BC2 comprises a semi-transparent reflection surface configured to combine two or more of the other trapping beams TB2, TB3. For example, the beam combiner BC2 may comprise a non-polarizing beam splitter in reverse configuration.

In the embodiment shown, the trapping beam optics comprise a trapping light source TL configured to provide trapping light for the trapping beams. The trapping light source can be integrated or separate from the trapping beam apparatus 100. In the embodiment shown, the detector beam optics AL comprise an alignment light source AL configured to provide light for the detector light beam AB having a wavelength AA that is distinct from a wavelength $\lambda$T of the trapping light. The alignment light source can be integrated or separate from the trapping beam apparatus 100. The alignment light source can also be integrated with the trapping light source. For example, light from a single light source can be converted e.g. by non-linear optics to provide beams of different wavelengths $\lambda$A, $\lambda$T.

In the embodiment shown, the detector beam optics AL are configured to provide the detector light beam AB with the second polarization ($\perp$). In another or further embodiment, the polarization filter PF comprises a polarizing beam splitter BS4 configured to receive light from the sample volume SV and split the light in a beam L11 having the first polarization (//), and a beam L12 having the second polarization. In another or further embodiment, the wavelength filter WF1 is disposed between the polarizing beam splitter BS4 and the second light detector PSD2 in the beam having the second polarization ($\perp$). By having the polarization of the detector beam AB orthogonal to that of the first optical trap, the polarization filter BS4 may simultaneously filter the alignment light from the beam L11 passed to the detector PSD2 without requiring a further wavelength filter.

In the embodiment shown, the apparatus comprises an objective lens OB disposed in a light path between the controllable mirrors M1, M2, M3 and the sample volume SV. The objective lens is configured to receive and focus the trapping beams into the sample volume SV to form the optical traps OT1,OT2. Alternatively, or in addition, focusing of the trapping beam can also be controlled or effected by other means, e.g. by telescopes T1, T2, and/or T3. In the embodiment shown, the apparatus comprises a telescope T1 disposed in a light path between the controllable mirrors M1, M2, M3 and the sample volume SV, and configured to receive and redirect the trapping beams TB1, TB2, TB3 towards the sample volume SV.

In one embodiment, e.g. as shown, the apparatus comprises at least four controllable mirrors M1, M2, M3, M4 for controlling a respective position X,Y of at least four optical traps OT1, OT2, OT3, OT4. In another or further embodiment, the light detectors PSD1,PSD2 are configured to monitor at least two of the optical traps by measuring the light with the first polarization (//) at a first detector PSD1 and measuring the light with wavelength $\lambda$A of the detector beam at a second detector PSD2. In another or further embodiment, the apparatus, comprises at least two controllable focus elements T2,T3, wherein a first focus element T2 is configured to control a position Z of a focal plane of a first and second OT1,OT2 of the optical traps, and wherein a second focus element T3 is configured to control a position Z of a focal plane of a third and fourth OT3,OT4 of the optical traps. The XYZ coordinate system is used herein for illustration purposes only to better explain the relative positioning and orientation. Of course also other reference frames and coordinate systems can be used without departing from the present scope In one embodiment (not shown), the detector beam optics are configured to overlap a first detector beam with a first of the other trapping beams and to overlap a second detector beam with a second of the other trapping beams in light paths before the respective controllable mirrors. The first and second detector beams may have a distinct wavelength and/or polarization with respect to each other. A plurality of wavelength and/or polarization filters can be configured (e.g. behind the sample volume) to isolate and individually measure the two or more detector beams.

Independent of any specific hardware, the present figure may also serve to illustrate a corresponding method for controlling a plurality of optical traps (OT1, OT2, OT3). In one embodiment, the method comprises providing a plurality of trapping beams (TB1, TB2, TB3). The method may further comprise redirecting the trapping beams (TB1, TB2, TB3) for individually controlling a respective position (X,Y) of a plurality of optical traps (OT1, OT2, OT3) formed by focusing of the redirected trapping beams in a sample volume (SV). The method may further comprise receiving light (L11,L20) from the sample volume (SV) corresponding to the optical traps. The method may further comprise overlapping a path of a detector beam (AB) with one of the trapping beams (TB3). In one embodiment, the detector beam has a distinct wavelength ($\lambda A$) from that of the overlapping trapping beam (TB3). The method may further comprise filtering the light from the sample volume according to wavelength, and measuring in a first channel only the filtered light having the wavelength ($\lambda A$) of the detector beam (AB).

In one embodiment the method comprises providing at least three trapping beams (TB1, TB2, TB3). In a further embodiment, a first of the trapping beams (TB1) is provided with a first polarization (//), and the other trapping beams (TB2,TB3) are provided with a second polarization ($\perp$), orthogonal to the first polarization (//). In one embodiment, the detector beam (AB) is overlapped with one of the trapping beams (TB3) having the second polarization ($\perp$) wherein the wavelength (XA) of the detector beam is distinct from that of the said other trapping beams (TB2, TB3). In one embodiment, a portion of light from the sample volume is filtered according to polarization and a second channel is used for measuring only the filtered light having the first polarization (//).

In the embodiment shown, an optional excitation beam EB is provided in the sample volume SV. An excitation of a fluorophore FL by the excitation light may results in a fluorescence response FR which can be recorded. The excitation beam EB and/or fluorescence response FR may be coupled into the sample by one or more dichroic mirrors, e.g. DM2 in the current embodiment. In the embodiment shown, an optional LED light source and camera CAM are used to further image the sample volume. For example the camera may comprise a CCD sensor. The imaging may comprise detection of beads held by the optical traps.

With reference to the specific embodiment shown, a polarizing beam splitter BS1 is configured to receive a first part L3 of the trapping light L1 and divide the said first part L3 into a pair of orthogonally polarized beams L4,L5. In the embodiment, a first controllable mirror M1 and a second controllable mirror M2 are provided, wherein each of the pair of controllable mirrors M1,M2 is configured to redirect a respective one of the pair of orthogonally polarized beams L4,L5 for manipulating a position X,Y of a first optical trap OT1 and a second optical trap OT2, respectively. A first beam combiner BC1 is configured to receive the first pair of orthogonally polarized beams L4,L5 and output a combined beam L7. An objective lens OB is configured to receive and focus the combined beam L7 into a sample volume SV to form the optical traps. A condenser lens CL is configured to collect the trapping light after having traversed the sample volume SV. A polarization filter BS4 is configured to split the collected trapping light L10 into a second pair of orthogonally polarized beams L11,L12. A pair of light detectors PSD1,PSD2 are each configured to receive a respective position X,Y of at least a part L11,L20 of the second pair of orthogonally polarized beams L11,L12 from the third beam splitter BS4. The shown apparatus comprises a third controllable mirror M3 configured to redirect a beam L14 for manipulating a third optical trap OT3. A fourth beam splitter BS4 is configured to split the trapping light L1 in the first part L3 that is sent to the first and second controllable mirrors M1,M2, and a second part L13 that is sent to the third controllable mirror M3. An alignment light source AL is configured to provide an detector light beam AB having a wavelength $\lambda A$ that is distinct from a wavelength $\lambda T$ of the trapping light L1. The detector light beam is aligned with the second part L11 of the trapping light L1 that is sent to and redirected by the third controllable mirror M3. A second beam combiner BC2 is configured to combine the light beams from the controllable mirrors M1, M2, M3, M4. A filter F2 is configured to pass the alignment light L20 to the detector PSD1 while filtering the trapping light.

Figure 3A:
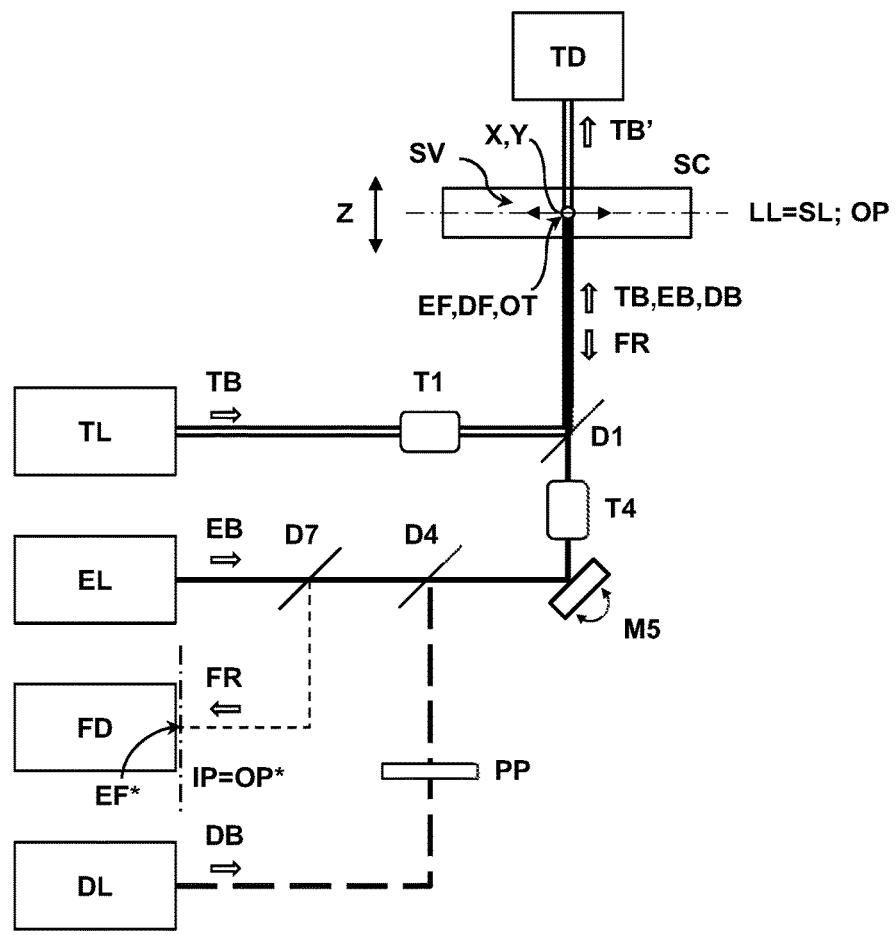
FIGS. 3A-3B schematically show a combination of optical trapping and fluorescence imaging.
Figure 3B:
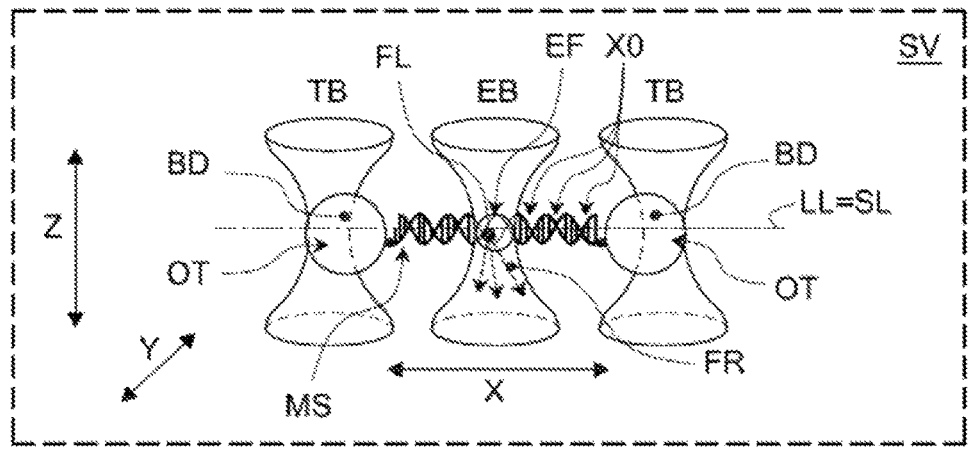

FIG. 3A illustrates an embodiment of a system and method for imaging one or more molecular strands which can be used in conjunction with the present trapping methods. FIG. 3B shows an illustration of the molecular strand MS. While a single strand is shown, the system may also image multiple strands sequentially or simultaneously.

According to one implementation, the method comprises providing a sample volume SV comprising one or more strands MS. An excitation beam EB is provided in the sample volume SV, e.g. having an excitation focus EF wherein an excitation of a fluorophore FL on the strand MS by the excitation beam or focus EF results in a fluorescence response FR when the excitation beam or focus EF coincides with the fluorophore FL. In one embodiment, the method comprises scanning the excitation focus EF in the sample volume SV. The method may comprise trapping parts of the strand MS in the sample volume SV and extending the strand MS along a trapping line LL. The method may comprise aligning the trapping line LL to coincide with the scanning line SL to have the scanning excitation focus EF coincide with the strand MS. The method may comprise recording the fluorescence response FR as a function of a plurality of distinct scanning positions X0 of the excitation focus EF along the scanning line SL.

In one embodiment, the method further comprises providing a depletion beam DB having a depletion focus DF with a depletion profile coinciding with an excitation profile of the excitation focus EF and causing stimulated emission depletion (STED) of the excitation of the fluorophore FL according to the depletion profile. The depletion profile has a minimum intensity at a centre of the excitation focus EF for reducing a profile size of the excited fluorophores (i.e. the emission profile of spontaneous fluorescence) by the stimulated emission depletion STED. Stimulated emission depletion (STED) microscopy is a process that provides super resolution by selectively deactivating fluorophores. In this way the diffraction limit of conventional microscopy can be bypassed to achieve better resolution.

As described herein, the method may comprise providing a plurality of optical traps OT trapping beads BD (e.g. microspheres) attached at multiple positions along one or more strands. The optical traps OT can be arranged to form multiple trapping lines between respective pairs of beads BD and may be used to facilitate the aligning of one or more trapping lines LL to coincide with one or more scanning lines SL.

In one embodiment, the fluorescence response FR is recorded at an image plane IP. The image plane IP is a conjugate focal plane OP* of an object plane OP in the sample volume SV. The object plane OP extends in the first direction X and a second direction Y. The excitation focus EF and trapping line LL are aligned to coincide with the object plane OP. A spatial pinhole is provided in the image plane IP. The spatial pinhole is aligned to coincide with a conjugate focal point EF* of the excitation focus EF for passing the fluorescence response FR through the spatial pinhole to a fluorescence detector FD.

By using point focus illumination, a specific part of the sample volume is illuminated, e.g. compared to wide field illumination. In this way a higher signal can be obtained due to a higher intensity at the focus and/or the resulting signal can be correlated to position of the focus. In the present examples, a fluorophore is illuminated by excitation light that is focussed on the molecular strand. Alternative to fluorescence, also other (optical) mechanisms and microscopy methods may be employed for probing the strand by means of point focus illumination, e.g. involving Raman spectroscopy such as CARS (coherent anti-stokes Raman spectroscopy) microscopy. Alternatively or in addition nonlinear optical processes can be used, e.g. two-photon excitation.

In one embodiment, the excitation focus EF is repeatedly scanned back and forth along one or more scanning lines, e.g. corresponding to one or more of the trapped molecular strands. The fluorescence response FR can be distinguished between a plurality of distinct scanning positions X0 along the scanning line SL and integrated over multiple scans and/or recorded as a function of time. Alternatively, or in addition, the excitation focus EF may concentrate scanning at a specific area, e.g. at or near a point of intersection between strands.

The method can be executed by a system for imaging a molecular strand MS. In one embodiment, the system may comprise a sample cell SC arranged for providing a sample volume SV comprising one or more strands MS. The system may further comprise an excitation light source EL arranged for providing an excitation beam EB having an excitation focus EF in the sample volume SV wherein an excitation of a fluorophore FL on the strand MS by the excitation focus EF results in a fluorescence response FR when the excitation focus EF coincides with the fluorophore FL. The system may further comprises a beam scanner MS arranged for scanning the excitation focus EF in the sample volume SV e.g. along a scanning line SL. The system further comprises a trap TL arranged for trapping an end or other part of the strand MS in the sample volume SV and extending the strand MS, e.g. along a trapping line LL parallel to the scanning line SL. The system further comprises a beam aligner (e.g. formed by steering mirror M3 in conjunction with telescopes T1 and/or T4) arranged for aligning a trapping line LL to coincide with a scanning line SL to have the scanning excitation focus EF coincide with the strand MS. The system may further comprise a fluorescence detector FD arranged for recording the fluorescence response FR as a function of a plurality of distinct scanning positions X0 of the excitation focus EF along the scanning line SL.

In one embodiment, the system further comprises a depletion light source DL and depletion beam optics M3,T3. The depletion light source DL and depletion beam optics M3,T3 are arranged for providing a depletion beam DB having a depletion focus DF with a depletion profile coinciding with an excitation profile of the excitation focus EF and causing stimulated emission depletion STED of the excitation of the fluorophore FL according to the depletion profile. The depletion profile has a minimum intensity at a centre of the excitation focus EF for reducing a size of the profile of excited fluorophores by the stimulated emission depletion STED.

In one embodiment, the system comprises a depletion focus shaper PP arranged for shaping the depletion profile wherein the depletion profile comprises a plane of minimum intensity extending perpendicular to the trapping line LL. The depletion focus shaper PP may e.g. comprise a phase plate arranged in the depletion beam DB for shaping the depletion focus profile e.g. as explained in an article by Klar et al. (Physical Review E, Volume 64, 066613, "Breaking Abbe's diffraction resolution limit in fluorescence microscopy with stimulated emission depletion beams of various shapes"). Also other means besides a phase plate for achieving a STED focus profile can be envisaged, e.g. crossing two coherent STED beams from different directions to provide a line shaped interference pattern between the beams, or through adaptive optics.

In one embodiment, the trap comprises a trapping light source TL and trapping beam optics (e.g. as described above) arranged for providing optical traps OT trapping beads BD attached at different positions, e.g. endings, of the strand MS. In use, the optical traps OT can be arranged along the first direction X to form a trapping line LL between the beads BD.

A fluorophore (or fluorochrome) is a fluorescent chemical compound that can re-emit light upon light excitation. For the present purposes, this may include e.g. quantum dots. The fluorophore typically absorbs light energy of a specific wavelength and re-emits light at a longer wavelength. In one embodiment, the molecular strand comprises and/or binds to a fluorophore to provide convenient visualization of the strand. In one embodiment, a fluorescent staining solutions is used to stain the molecular strand. Any known or to be developed staining solutions can be used. Alternatively or in addition to a staining solution, the molecular strand may also be fluorescent itself, e.g. comprise one or more fluorescent parts. Alternatively or in addition fluorescent reactants to be studied, e.g. fluorescent proteins, may bind to the molecular strand. For example, the strand may thus be imaged directly through its own fluorescence or indirectly by fluorescent molecules including fluorophores binding thereto.

In the shown embodiment, beams TB, EB, FR, and DB are combined or split up using dichroic mirrors D1, D4, D7. Of course also other means can be used for combining/splitting the beams, e.g. fibres and/or diffracting/refracting optics such as prisms and gratings. In the shown embodiment, the trapping beams TB are detected by trapping beam detector TD, e.g. for determining a force exerted on the strand. Such detector may also be omitted or switched off once the strand is trapped.

Figure 4A:
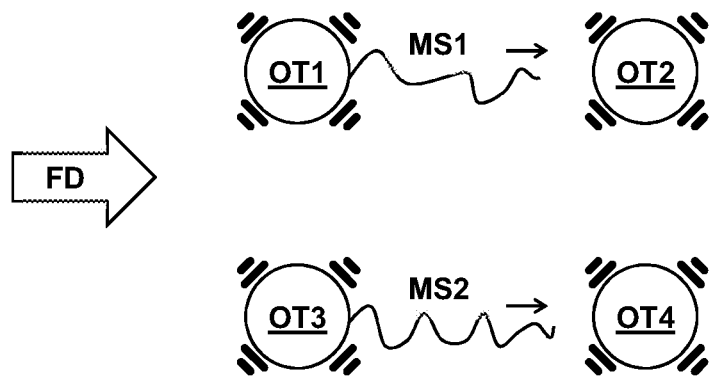
FIGS. 4A-4C schematically shows a method for simultaneous trapping of two molecular strands.
Figure 4A:
Figure 4A:
Figure 4B:
Figure 4B:
Figure 4C:
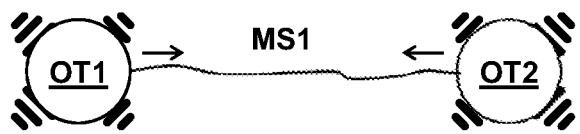
Figure 4C:

FIGS. 4A-4C show a method for positioning a first molecular strand MS1 with respect to a second molecular strand MS2, which can be implemented e.g. using the present methods and systems.

In the figures, the method comprises providing four trapping beams OT1, OT2, OT3, OT4 as described herein. Two positions along a length of the first molecular strand MS1 are trapped using the first and second optical traps OT1,OT2. Two positions along a length of the second molecular strand MS2 are trapped using the third and fourth optical traps OT3,OT4. Of course the traps may also be combined with the strands in other configuration than shown in the figure, e.g. strand MS1 can be trapped by OT1 and OT3 while MS2 is can be trapped by OT2 and OT4.

Advantageously, the force on or by the molecular strands can be monitored as follows. For example, the trapping beam of the first or second optical trap OT1,OT2 has the first polarization (//) distinct from the other trapping beams for measuring a force on the first molecular strand MS1 by selectively measuring light having the first polarization (//). Additionally, the trapping beam of the third or fourth optical trap OT3,OT4 is overlapped with the detector beam for measuring a force on the second molecular strand MS2 by selectively measuring light having the wavelength of the detector light beam.

As shown in FIG. 4A, the method may comprise trapping a first position of the first molecular strand MS1 with the first optical trap OT1, trapping a first position of the second molecular strand MS2 with the third optical trap OT3, and providing a flow FD to stretch the first and second molecular strands MS1,MS2. In one embodiment, the second and fourth optical traps OT2,OT4 are positioned downstream of the flow FD to capture another part of the respective strand as shown in FIG. 4B. In one embodiment, as shown in FIG. 4C, the first and second optical traps OT1,OT2 apart while measuring the light having the first polarization (//) for measuring a force between the first and second optical traps OT1,OT2 on the first molecular strand MS1. In another or further embodiment, the third and fourth optical traps OT3, OT4 are moved apart while measuring the light having the wavelength of the detector beam for measuring a force between the third and fourth optical traps OT3,OT4 on the second molecular strand MS2.

Figure 5A:
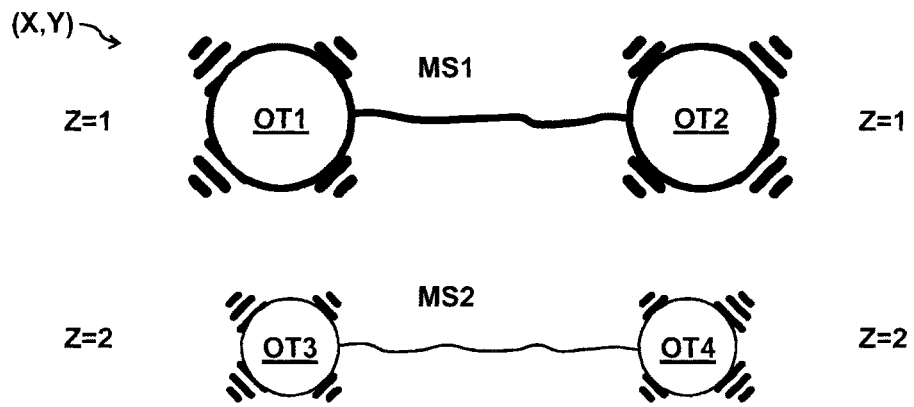
FIGS. 5A-5C schematically shows a method for crossing of two molecular strands.
Figure 5B:
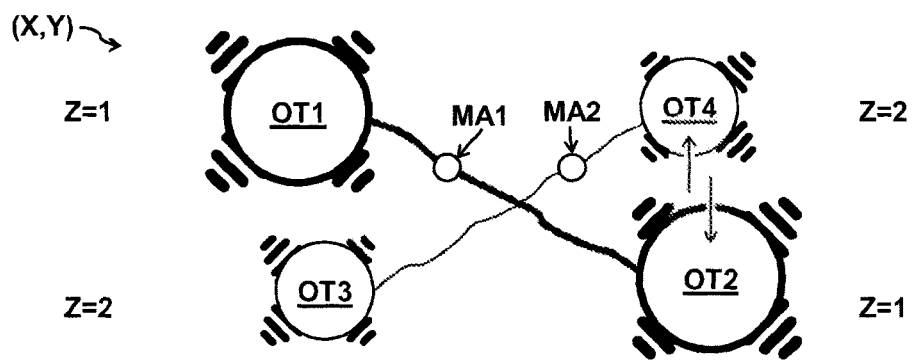
Figure 5C:
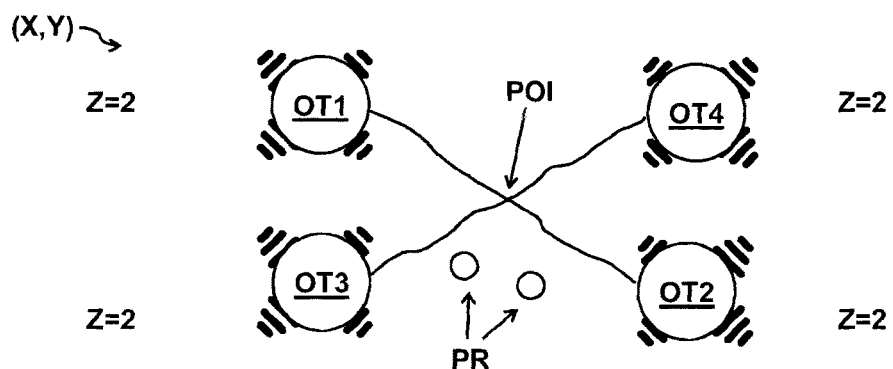

FIGS. 5A-5C show a method for crossing first molecular strand MS1 with the second molecular strand MS2.

In the embodiment shown in FIG. 5A, a focal plane of the first and second optical traps OT1,OT2 is set to a first depth Z=1 in the sample volume, while a focal plane of the second and third optical traps OT3,OT4 is set to a second depth Z=2 in the sample volume SV distinct from the first depth Z=1. In the embodiment shown in FIG. 5B, one or more of the optical traps is moved in a lateral direction X,Y within the respective focal plane until the length of the first molecular strand MS1 crosses with the length of the second molecular strand MS2 in a projected view on one of the focal planes. In the embodiment shown in FIG. 5C, a distance Z between the focal planes of the first and second molecular strands MS1,MS2 is lowered. Also other configurations are possible, e.g. wherein the focal plane of only one of the traps is varied while the focal planes of the other traps are held constant.

In one embodiment, the distance Z between the focal planes is lowered to have the first and second molecular strands MS1,MS2 intersect with each other. In one embodiment, the lateral positions X,Y of the first and optical traps OT1,OT2 are controlled with respect to the lateral positions X,Y of the third and fourth optical traps OT3,OT3, to have a point of intersection POI at a predetermined position of the first molecular strand MS1 and at a predetermined position of the second molecular strand MS2.

In one embodiment, further molecules PR (e.g. proteins) are provided in the sample volume SV interacting with the first and/or second molecular strands MS1,MS2.

In one embodiment, a first fluorescent marker MA1 is provided at a position along the first molecular strand MS1 and a second fluorescent marker MA2 is provided at a position along the second molecular strand MS2. In a further embodiment, a fluorescent image is recorded to measure a relative position of the first and second fluorescent markers MA1,MA2. In a further embodiment, the optical traps are moved to align the first molecular strand MS1 with respect to the second molecular strand MS2 based on the measured relative position of the first and second fluorescent markers MA1,MA2. Of course also other methods of aligning one or more molecular strands can be envisaged.

For the purpose of clarity and a concise description, features are described herein as part of the same or separate embodiments, however, it will be appreciated that the scope of the invention may include embodiments having combinations of all or some of the features described. It will be appreciated that, while example embodiments were shown for methods and systems for trapping and monitoring molecular strands, also alternative ways may be envisaged by those skilled in the art having the benefit of the present disclosure for achieving similar functions and results. E.g. optical and/or electrical components may be combined or split up into one or more alternative components, e.g. curved mirrors instead or in addition to lenses, different detectors or light sources, et cetera. The various elements of the embodiments as discussed and shown, offer certain advantages, such as high precision and control geared to the imaging of one or more molecule sized strands. Of course, it is to be appreciated that any one of the above embodiments or processes may be combined with one or more other embodiments or processes to provide even further improvements in finding and matching designs and advantages. It is appreciated that this disclosure offers particular advantages to the study of molecular biology and in general can be applied when manipulated and/or monitoring molecular sized objects.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. An apparatus for controlling a plurality of optical traps, the apparatus comprising
    trapping beam optics configured to provide a plurality of simultaneously active trapping beams,
    controllable mirrors configured to receive and redirect the trapping beams for individually controlling a respective position of a plurality of simultaneously active optical traps formed by focusing of the redirected trapping beams in a sample volume;
    light detectors configured to receive light from the sample volume corresponding to the optical traps;
    detector beam optics configured to overlap a path of a detector beam with one of the trapping beams, wherein the detector beam has a distinct wavelength from that of the overlapping trapping beam; and
    a wavelength filter disposed in a light path between the sample volume and a first light detector, and configured to pass light with the wavelength of the detector beam to the first light detector; wherein
    the trapping beam optics are configured to provide at least three simultaneously active trapping beams, wherein a first of the trapping beams is provided with a first polarization, and the other trapping beams are provided with a second polarization, orthogonal to the first polarization;
    the detector beam optics are configured to overlap the detector beam with one of the other trapping beams having the second polarization wherein the wavelength of the detector beam is distinct from that of the said other trapping beams; and
    the apparatus comprises a polarization filter disposed in a light path between the sample volume and a second light detector, and configured to pass light with the first polarization to the second light detector;
    wherein the light detectors are configured to monitor at least two of the optical traps by measuring the light with the wavelength of the detector beam at the first detector and measuring the light with the first polarization at the second light detector.

2. The apparatus according to claim 1, comprising a non-polarising beam combiner configured to combine two or more trapping beams having the same wavelength and polarization.

3. The apparatus according to claim 1, wherein the detector beam optics comprises a beam combiner disposed in a light path between a trapping light source and at least one of the controllable mirrors corresponding to one of the other trapping beams with the second polarization wherein the beam combiner comprises a reflective surface configured to overlap a transmission of one of the alignment or trapping beam with a reflection of the other of the alignment or trapping beam.

4. The apparatus according to claim 1, wherein the trapping beam optics comprise a trapping light source configured to provide trapping light for the trapping beams; and wherein the detector beam optics comprise an alignment light source configured to provide light for the detector beam having a wavelength that is distinct from a wavelength of the trapping light.

5. The apparatus according to claim 1, comprising at least four optical traps.

6. The apparatus according to claim 5, comprising a controllable focus element configured to control a relative position of a focal plane of a first of the optical traps with respect to a focal plane of a third and/or fourth of the optical traps.

7. The apparatus according to claim 1, comprising
    an excitation light source configured to provide an excitation beam to the sample volume wherein an excitation of a fluorophore on the molecular strand by the excitation beam results in a fluorescence response; and
    a fluorescence detector arranged for recording the fluorescence response.

8. A method for controlling a plurality of optical traps, the method comprising
    providing at least three simultaneously active trapping beams, wherein a first of the trapping beams is provided with a first polarization, and the other trapping beams are provided with a second polarization, orthogonal to the first polarization;
    redirecting the trapping beams for individually controlling a respective position of at least three simultaneously active optical traps formed by focusing of the redirected trapping beams in a sample volume;
    overlapping a path of a detector beam with one of the trapping beams having the second polarization, wherein the detector beam has a distinct wavelength from that of the overlapping trapping beam;
    in a first detection channel, filtering the light from the sample volume according to wavelength, and measuring only the filtered light having the wavelength of the detector beam;
    in a second detection channel, filtering the light from the sample volume according to polarization and measuring only the filtered light having the first polarization; and
    monitoring at least two of the optical traps by measuring the light with the wavelength of the detector beam in the first detection channel and measuring the light with the first polarization in the second detection channel.

9. A method for positioning a first molecular strand with respect to a second molecular strand, the method comprising
    providing at least four simultaneously active trapping beams according to claim 8;
    trapping two positions along a length of the first molecular strand using a first pair of the optical traps, wherein the trapping beam of one of the first pair of optical traps has the first polarization distinct from the other trapping beams for measuring a force on the first molecular strand by selectively measuring light having the first polarization;
    trapping two positions along a length of the second molecular strand using a second pair of the optical traps, wherein the trapping beam one of the second pair of optical traps is overlapped with the detector beam for measuring a force on the second molecular strand by selectively measuring light having the wavelength of the detector light beam.

10. The method according to claim 9, comprising
    trapping a first position of the first molecular strand with the first optical trap;
    trapping a first position of the second molecular strand;
    providing a flow to stretch the first and second molecular strands;
    positioning the second and fourth optical traps downstream of the flow;

moving the first and second optical traps apart while measuring the light having the first polarization;

moving the third and fourth optical traps apart while measuring the light having the wavelength of the detector beam.

11. The method according to claim 9, comprising moving the optical traps for crossing the length of the first molecular strand with the length of the second molecular strand.

12. The method according to claim 9, setting a focal plane of the first and/or second optical traps to a first depth in the sample volume;

setting a focal plane of the third and/or fourth optical traps to a second depth in the sample volume distinct from the first depth;

moving one or more of the optical traps in a lateral direction within the respective focal plane until the length of the first molecular strand crosses with the length of the second molecular strand in a projected view on one of the focal planes;

lowering a distance between the focal planes of optical traps.

13. The method according to claim 9, wherein the lateral positions of the first pair of optical traps are controlled with respect to the lateral positions of the second pair of optical traps, to have a point of intersection at a predetermined position of the first molecular strand and at a predetermined position of the second molecular strand.

14. The method according to claim 13, comprising detecting an interaction between the molecular strands by bringing the strands together and moving the strands apart while measuring a force between the strands on the optical traps.

15. The method according to claim 13, comprising adding fluorescently labelled proteins in a sample volume of the molecular strands and detecting an interaction between the molecular strands by a binding of the fluorescently labelled proteins at the point of intersection.

16. The method according to claim 9, comprising providing a first fluorescent marker at a position along the first molecular strand;

providing a second fluorescent marker at a position along the second molecular strand;

recording a fluorescent image to measure a relative position of the first and second fluorescent markers;

moving the optical traps to align the first molecular strand with respect to the second molecular strand based on the measured relative position of the first and second fluorescent markers.

* * * * *